United States Patent [19]

Tanabe et al.

[11] Patent Number: 5,194,625
[45] Date of Patent: Mar. 16, 1993

[54] PROCESS FOR PRODUCTION OF ALPHA-KETO ACID/AMINO ACID SALT COMPOUNDS

[75] Inventors: Toshiya Tanabe; Shin-ichi Kishimoto, both of Kawasaki, Japan

[73] Assignee: Ajinomoto Co., Inc., Tokyo, Japan

[21] Appl. No.: 450,089

[22] Filed: Dec. 13, 1989

[30] Foreign Application Priority Data

Dec. 27, 1988 [JP] Japan .................................. 63-330688

[51] Int. Cl.$^5$ .................. C07C 233/64; C07C 277/08; C07C 59/185; C07C 229/26
[52] U.S. Cl. .................... 548/544; 562/459; 562/561; 562/562; 562/445; 562/570; 562/575; 562/559; 562/444; 562/556; 562/557
[58] Field of Search ................ 548/344; 562/459, 561, 562/562

[56] References Cited

U.S. PATENT DOCUMENTS

| | | | |
|---|---|---|---|
| 4,228,099 | 3/1978 | Walser | 424/311 |
| 4,296,127 | 4/1979 | Walser | 424/319 |
| 4,320,146 | 10/1980 | Walser | 424/319 |
| 4,352,814 | 9/1981 | Walser | 424/311 |
| 4,622,413 | 11/1986 | Krogh | 548/344 |

FOREIGN PATENT DOCUMENTS

| | | | |
|---|---|---|---|
| 1432756 | 2/1966 | France | 548/344 |
| 2222370 | 10/1974 | France | 548/344 |
| 2017094 | 10/1979 | United Kingdom | 548/344 |

OTHER PUBLICATIONS

*Chem. Rev.* 1983, 83, 321–358; Cooper, Arthur J. L., et al., "Synthesis and Properties of the a–Keto Acids".
*J. Electrochem.*, Soc., 131, (8), 1942 (1984); M. Sakaguchi, et al., "The Phase–Transition Phenomenon in a Sodium Sulfate Crystal".

*Primary Examiner*—Floyd D. Higel
*Attorney, Agent, or Firm*—Oblon, Spivak, McClelland, Maier & Neustadt

[57] ABSTRACT

A compound of the formula:

$$AN/xS$$

wherein A represents an amino acid, N represents an α-keto acid, S represents a lower alcohol or acetone; and x ranges from 0.1 to 3.

3 Claims, 4 Drawing Sheets

PROCESS FOR PRODUCTION OF ALPHA-KETO ACID/AMINO ACID SALT COMPOUNDS

BACKGROUND OF THE INVENTION

1. Field of the Invention

The present invention relates to an α-keto acid/amino acid salt compound and to a process for its production.

2. Description of the Background

Amino acid salts of α-keto acids are known to be effective for the treatment of patients afflicated with renal disorders caused by uremia, and the like, and with hepatic disorders caused by hyperammoniemia, and the like. The salts are obtained in crystalline form and anhydrous crystals or crystals containing a very small amount of water have been prepared (Japanese Patent Publication Nos. 58-38421 and 60-24094).

U.S. Pat. Nos. 4,320,146; 4,228,099; 4,296,127 and 4,352,814 disclose pharmaceutically useful anhydrous, as well as hydrated amino acid salts of α-keto acids. These salts are formed from the likes of such amino acids as arginine, ornithine, histidine, lysine and threonine. The salts can be represented by the formula: AN·χH$_2$O, wherein A represents an amino acid, N represents an α-keto acid and χ ranges from 0 to 1.

Amino acid salts of α-keto acids are very highly soluble in water to the extent of 50 to 70 wt. %. Accordingly, an advantage of this high solubility property is that the salts can be administered with a relatively small amount of water to a subject. However, difficulties in crystallization of the salt result in serious obstacles during production.

In the past crystals of the amino acid salts of α-keto acids have been obtained by freeze drying, crystallization from a solvent and the like. From the point of view of industrial production, solvent crystallization of the salt is preferred. However, when solvent crystallization is performed, it is extremely difficult to remove the solvent. In particular, since the amino acid salts of α-keto acids are used as drugs for treating patients having renal disorders or hepatic disorders, strict standards are required which place limits on the amount of residual solvent in the crystals. Thus very long times are required for drying the crystals. Furthermore, the amino acid salts of α-keto acids are sensitive to heat and are likely to color so that drying should be performed at a very low temperature in vacuum. Even under such conditions, the dissolution state of the salts deteriorates depending upon the particular salt. A need therefore continues to exist for an improved and simplified method of preparing the amino acid salts of α-keto acids.

SUMMARY OF THE INVENTION

Accordingly, one object of the present invention is to provide a method for preparing amino acid salts of α-keto acids which are effective for the treatment of renal and hepatic disorders in less numbers of steps in a short period of time without causing decomposition or denaturation of the salts at high temperatures.

Briefly, this object and other objects of the present invention as hereinafter will become more readily apparent are attained by an alcohol or ketone adduct of an α-keto acid/amino acid of the formula: AN/xS, wherein A represents an amino acid; N represents an α-keto acid; S represents a lower alcohol or acetone; and x varies between 0.1 and 3. The adduct is a solvated compound which contains a solvent in the crystals. The crystals can be obtained by solvent crystallization.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
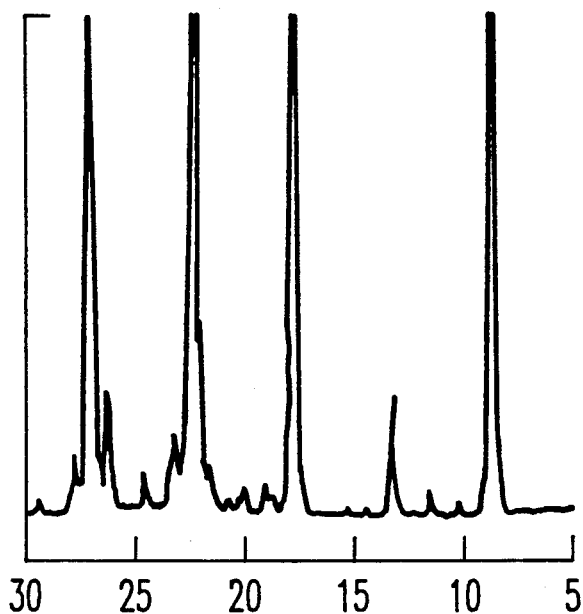
FIG. 1 is an X-ray diffraction pattern of EtOH-solvated His/KIC crystals obtained in Example 1.

In the present invention solvated crystals of an α-keto acid/amino acid salt are obtained as the same precipitate from a solvent containing solution. Normally, the mole ratio of amino acid to α-keto acid is about 1:1. The advantage of the crystallization technique of the present invention in comparison to the crystallization of the salt from water is that crystals of said product are obtained in higher yield. Further, the crystallizability of the solvated salt of the present invention is better than that of the hydrated salt known in the prior art.

The crystals of the solvated compounds of the amino acid salts of an α-keto acid are transformed to desolvated salt compounds under the conditions of an absolute humidity of 0.003 to 17.0 kg-H$_2$O/kg-dry air. This desolvation of the salt crystals results in the production of desolvated salt in high yields without decomposition or denaturation of the salt thereby reducing production costs.

When the concentration of solvent is reduced upon the crystallization of the α-keto acid/amino acid salt compound, it is possible to isolate non-solvated crystals. However, the amino acid salts of α-keto acids have a very high solubility in water and the solubility is not lowered unit the solvent concentration becomes very low so that the yield is markedly reduced in crystallization in a low solvent concentration. In this regard, according to the process of the present invention, crystallization can be effected even at high solvent concentration and it is possible to increase the yield.

The amino acid salts of α-keto acids which are used in the present invention are not particularly limited. Suitable examples of α-keto acids include α-keto-isocaproic acid (KIC), α-keto isovaleric acid (KIV), α-keto-β-methylvaleric acid, pyruvic acid, phenylpyruvic acid, and the like. The amino acids are basic or neutral amino acids which are capable of forming salts with α-keto acids, for example, histidine (HIS), lysine, ornithine (Orn), arginine, and the like. Suitable examples of solvent include a lower alcohol such as methanol, ethanol, n-propanol, isopropanol, or the like or those solvents which are miscible with water such as acetone, or the like.

The crystallization of the solvated α-keto acid/amino acid salts can be carried out by adding an aqueous solution of the α-keto acid/amino salts to a solvent or to a mixture of water and the solvent in a conventional manner and allowing the resulting mixture to cool. That is, the α-keto acid is added to a suspension or aqueous solution of an amino acid to prepare an aqueous solution of the α-keto acid/amino acid salt compound. If necessary, an adsorbent such as activated charcoal, activated alumina, bentonite, or the like is added to the mixture to decolor the solution or suspension and the filtrate is concentrated. The concentrate is added to the solvent or its mixture with water. The resulting mixture is cooled to achieve crystallization.

The concentration of the aqueous solution of α-keto acid/amino acid salt compound varies depending upon the particular compound, but is appropriately in a range of 50 to 75%. In order to increase the yield of crystallization, it is preferred to use the solvent in high concentration.

Analysis by X-ray diffraction reveals that the thus crystallized solvated α-keto acid/amino acid salt compound takes a crystalline shape which is obviously different from the crystalline shapes of the compound prior to and after removal of the solvent and that the solvent present in the crystals does not merely adhere to the crystals but is incorporated within the lattice of the crystals as the solvated product. It has also been discovered that for removal of the solvent, it is necessary to transform the crystal lattice and after transformation of the crystals, it is extremely difficult to remove the residual solvent. Further even for those compounds which exhibit no crystal transformation such as lysine/α-keto-β-methyl-valeric acid (Lys/KMV), or the like, it takes a long time to remove residual solvent such as by conventional drying in vacuum.

In the present invention, removal of the solvent can be achieved in a short period of time simply by placing the crystals under an atmosphere of appropriate humidity under relatively mild conditions under normal pressure. It is sufficient that the humidity be set at 0.003 to 17.0 kg-$H_2O$/kg-dry air, regardless of the pressure. The temperature does not very greatly affect the crystal transformation, but is desirably below 60° C., since the amino acid salts of α-keto acids are weak when heated and tend to be readily colored.

Having now generally described this invention, a further understanding can be obtained by reference to certain specific examples which are provided herein for purposes of illustration only and are not intended to be limiting unless otherwise specified.

EXAMPLE 1

Water (about 30 ml) sufficient to suspend 0.1 mol of histidine (about 15.5 g) was placed in a container and 10 g of α-keto-isocaproic acid was added thereto. The mixture changed from a slurry to a solution by complete dissolution of the acid.

To the solution was added 3 g of α-keto-isocaproic acid and the pH of the mixture was adjusted to 4.0. After 1 g of activated charcoal was added to the mixture the mixture was stirred and decolored and then filtered. The filtrate was concentrated to about 47 g. The concentrate was added to 170 ml of ethanol (ethanol/water=9.2 [v/v]). After allowing the solution to stand at 25° C. overnight, the crystals were separated and dried at 40° C. for a day under 10 torr to give 31 g of about 0.9 ethanol-solvated crystals of histidine α-keto-isocaproate (ethanol content of 13%; crystallization rate of 94%).

The crystals were allowed to stand at 40° C. in an atmosphere having a relative humidity of 80% (absolute humidity of 0.03 kg-$H_2O$/kg-dry air) under normal pressure. About 4 hours later, the crystals having an ethanol content of 320 ppm were obtained.

Figure 2:
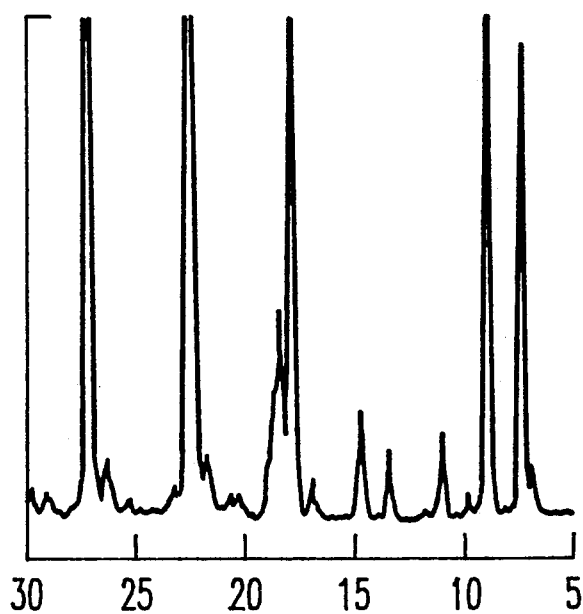
FIG. 2 is an X-ray diffraction pattern taken an hour after the removal of EtOH from the EtOH-solvated His/KIC crystals of FIG. 1.
Figure 3:
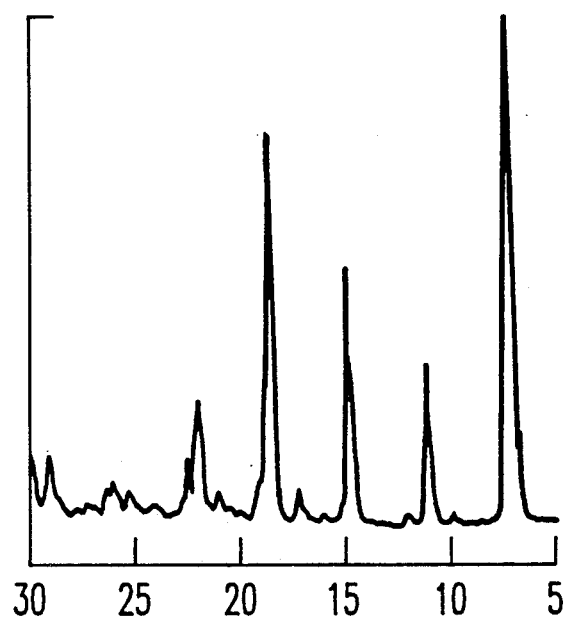
FIG. 3 is an X-ray diffraction pattern after completion of the removal of EtOH from the EtOH-solvated His/KIC crystals of FIG. 1.

The results of X-ray diffraction patterns are shown in FIGS. 1 through 3. The X-ray diffraction patterns of the crystals are obviously different before and after the removal of ethanol, indicating that ethanol does not merely adhere to but is incorporated in the crystal lattice.

Crystal transformation was completed in about 2.5 hours. In this case, 0.2% of the residual ethanol was noted, but this residual ethanol could finally be removed.

The above procedure was performed at various temperatures and relative humidities for removing ethanol from the crystals. The results are shown in Table 1.

TABLE 1

| Removal of Ethanol from L-Histidine α-Keto-isocaproate | | | | |
|---|---|---|---|---|
| Temperature [°C.] | Relative Humidity [%] | Absolute Humidity [kg-$H_2O$/kg-dry air] | Time [hr] | Residual EtOH [ppm] |
| 40 | 80 | 0.039 | 3 | 320 |
|  | 60 | 0.029 | 3 | 350 |
|  | 40 | 0.020 | 24 | 90 |
|  | 30 | 0.015 | 24 | 130 |
|  | 25 | 0.005 | 48 | 90 |
| 25 | 60 | 0.012 | 24 | 140 |

COMPARATIVE EXAMPLE 1

Figure 4:
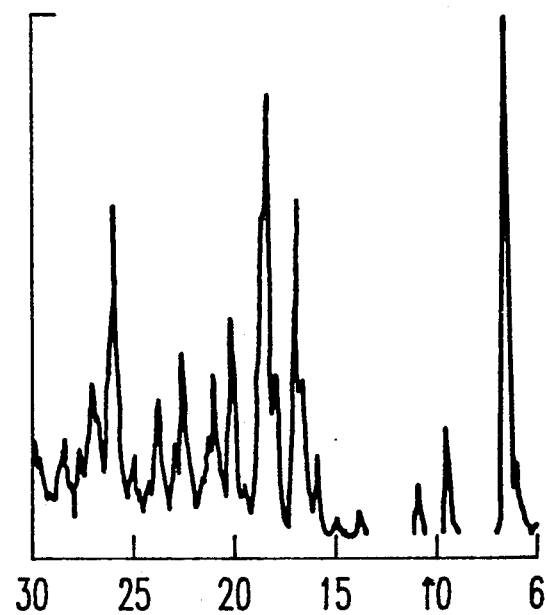
FIG. 4 is an X-ray diffraction pattern of EtOH-non-solvated His/KIC crystals obtained in Comparative Example 1.

A concentrated solution of histidine α-keto-isocaproate obtained in a manner similar to Example 1 was added to 22 ml of EtOH (ethanol/water=1.19 [v/v]). After allowing the solution to stand overnight, crystals separated and were dried at 40° C. for a day under 10 torr to give 15.1 g of ethanol-non-solvated crystals of histidine α-keto-isocaproate. The results of an X-ray diffraction pattern are shown in FIG. 4. The crystallization rate was 53% in this case.

EXAMPLE 2

In 60 ml of water was dissolved 0.1 mol of L-ornithine (about 13.2 g) and about 11.6 g of α-keto-isovaleric acid was added to the solution to adjust the pH to 5.9. After about 1 g of activated charcoal was added to decolor the solution, the filtrate was concentrated to about 41 g. The concentrate was added to 140 ml of ethanol (ethanol/water=8.6 [v/v]). After allowing the resulting solution to stand at 5° C. overnight, the crystals were separated. The thus obtained ethanol-solvated crystals were dried at 40° C. for 4 hours under 35 torr to remove the adhered ethanol. Then, the crystals were allowed to stand in an atmosphere of a relative humidity of 60% under normal pressure. Two hours after allowing the crystals to stand under the controlled humidity conditions, the residual ethanol was 450 ppm.

COMPARATIVE EXAMPLE 2

L-Ornithine α-keto isocaproate obtained in a manner similar to Example 2 was dried in vacuum under the conditions of 40° C. and 35 torr. The residual EtOH was 3.9% after 12 hours passed.

EXAMPLE 3

Figure 5:
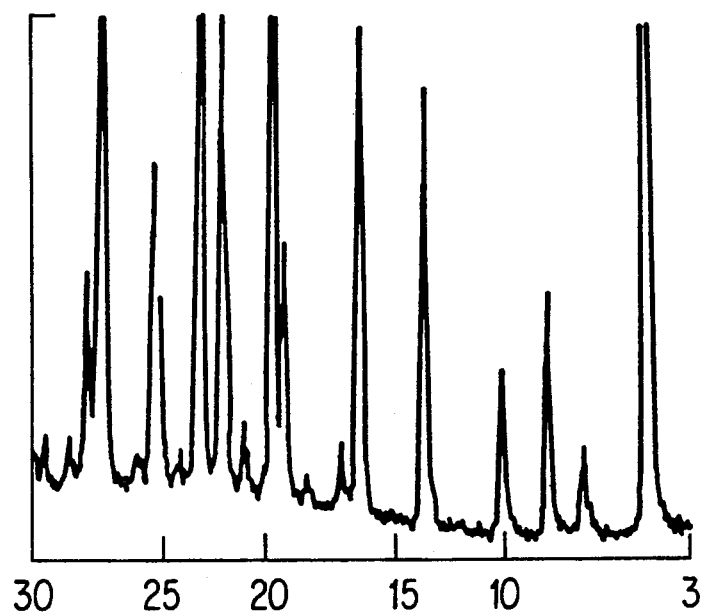
FIGS. 5 and 6 are X-ray diffraction patterns of non-solvated Orn/KIV crystals and acetone-solvated Orn/KIV crystals obtained in Example 3.
Figure 6:
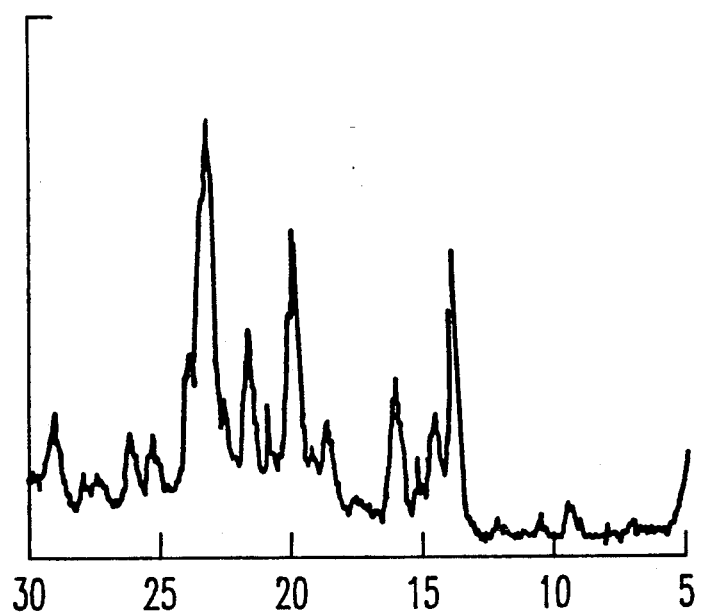

In 60 ml of water was dissolved 0.1 mol of L-ornithine (about 13.2 g) and about 11.6 g of α-keto-isovaleric acid was added to the solution to adjust the pH to 5.9. After about 1 g of activated charcoal was added to the mixture to decolor the solution, the filtrate was concentrated to about 41 g. The concentrate was added to about 120 ml of acetone. After allowing the solution to stand at 5° C. overnight, the crystals were separated. The thus obtained acetone-solvated crystals were dried at 40° C. for an hour under 35 torr to remove the adhered acetone. Then, the crystals were allowed to stand in an atmosphere having a relative humidity of 60% under normal pressure. Two hours later the residual acetone level reached 90 ppm. The results of X-ray diffraction analysis are shown in FIGS. 5 and 6.

COMPARATIVE EXAMPLE 3

L-Ornithine α-keto isovaleric acid obtained in a manner similar to Example 3 was dried in vacuum under conditions at 40° C. and 35 torr. The residual acetone was 0.5% after 5 hours had passed.

EXAMPLE 4

In 60 ml of water was dissolved 0.1 mol of L-ornithine (about 13.2 g) and about 13 g of α-keto-isocaproic acid was added to the solution to adjust the pH to 5.7. After about 1 g of activated charcoal was added to decolor the solution, the filtrate was concentrated to about 43 g. The concentrate was added to 150 ml of ethanol. After allowing the solution to stand at 5° C. overnight, the crystals were separated. The thus obtained ethanol-solvated crystals were dried at 40° C. for 4 hours under 35 torr to remove the adhered ethanol. Then, the crystals were allowed to stand under atmospheric conditions of relative humidity of 70% under normal pressure. Two hours after allowing the crystals to stand under the controlled humidity conditions, the residual ethanol content reached 26 ppm.

COMPARATIVE EXAMPLE 4

L-Ornithine α-keto-isocaproate, obtained in a manner similar to Example 4, was dried in vacuum under conditions of 40° C. and 35 torr. The residual ethanol content was 1.1% after 12 hours had passed.

EXAMPLE 5

Figure 7:
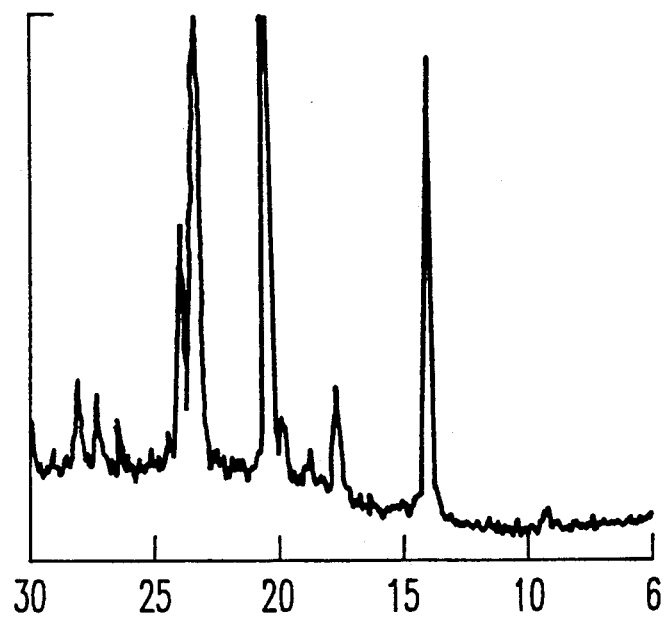
FIGS. 7 and 8 are X-ray diffraction patterns of non-solvated Orn/KIC crystals and isopropyl alcohol-solvated Orn/KIC crystals obtained in Example 3.
Figure 8:
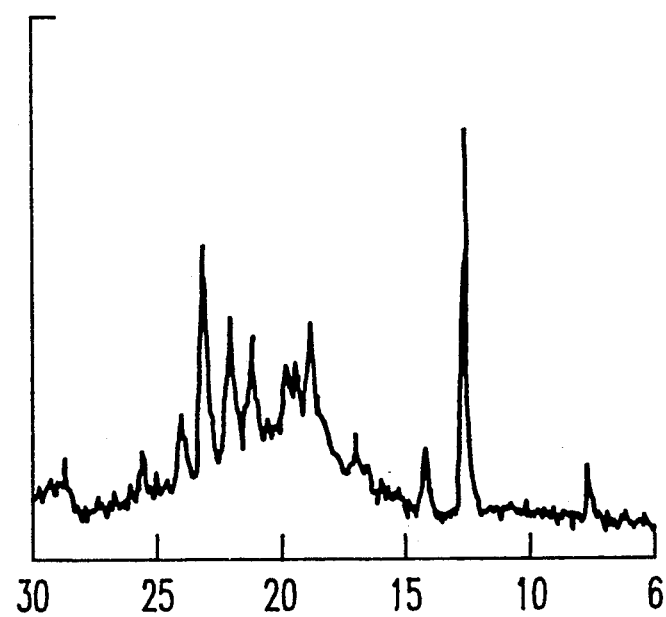

In 60 ml of water was dissolved 0.1 mol of L-ornithine (about 13.2 g) and about 13 g of α-keto-isocaproic acid was added to the solution to adjust the pH to 5.7. After about 1 g of activated charcoal was added to decolor the solution, the filtrate was concentrated to about 43 g. The concentrate was added to 150 ml of isopropanol. After allowing the solution to stand at 5° C. overnight, the crystals were separated. The thus obtained isopropanol-solvated crystals were dried at 40° C. for 4 hours under 35 torr to remove the adhered isopropanol. Then, the crystals were allowed to stand under atmospheric conditions of a relative humidity of 70% under controlled humidity conditions, the residual isopropanol reached 110 ppm. The results of X-ray diffraction patterns are shown in FIGS. 7 and 8.

COMPARATIVE EXAMPLE 5

L-Ornithine α-keto isocaproate obtained in a manner similar to Example 5 was dried in vacuum under conditions of 40° C. and 35 torr. The residual isopropanol was 2.0% after 18 hours passed.

EXAMPLE 6

In 60 ml of water was dissolved 0.1 mol of L-lysine (about 14.6 g) and about 13 g of o-keto-β-methylvaleric acid was added to the solution to adjust the pH to 6.0. After abut 1 g of activated charcoal was added to the mixture to decolor the solution, the filtrate was concentrated to about 46 g. The concentrate was added to about 350 ml of ethanol. After allowing the solution to stand at 5° C. overnight, the crystals were separated. The thus obtained ethanol-solvated crystals were dried at 30° C. for 4 hours under 35 torr to remove the adhered ethanol. Then, the crystals were allowed to stand at a relative humidity of 60%. Three hours later, the residual ethanol level reached 250 ppm.

COMPARATIVE EXAMPLE 6

L-Lysine α-keto-β-methylvaleric acid, obtained in a manner similar to Example 6, was dried in vacuum under conditions of 40° C. and 35 torr. It took 8 hours until the residual ethanol reached a level almost equal to that of Example 5.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for production of an α-keto acid/amino acid salt compound, which consists essentially of:

transforming crystals of a compound of the formula:

AN/xS wherein A represents an amino acid selected from the group consisting of histidine, ornithine, lysine and arginine, N represents an α-keto acid selected from the group consisting of α-keto-isocaproic acid, α-keto isovaleric acid, α-keto-β-methylvaleric acid, pyruvic acid and phenylpyruvic acid, S represents a lower alcohol or acetone, and x is 0.1 to 3, to desolvated salt compounds by placing the crystals of the formula AN/xS under an atmosphere of air having a humidity of 0.003 to 17.0 kg-$H_2O$/kg-dry air.

2. The process of claim 1, wherein the temperature of the transformation ranges below 60° C.

3. The process of claim 1, wherein the pressure of said atmosphere of air is normal atmospheric pressure.

* * * * *

UNITED STATES PATENT AND TRADEMARK OFFICE
CERTIFICATE OF CORRECTION

PATENT NO. : 5,194,625
DATED : Mar. 16, 1993
INVENTOR(S) : Toshiya Tanabe, et al It is certified that error appears in the above-indentified patent and that said Letters Patent is hereby corrected as shown below:

Column 1, line 11, "afflicated" should read --afflicted--.

Column 2, line 54, "unit" should read --until--.

Column 6, line 12, "o-keto-$\beta$" should read --$\alpha$-keto-$\beta$--;
          line 14, "abut" should read --about--.

Signed and Sealed this

Sixth Day of September, 1994

Attest:

BRUCE LEHMAN

Attesting Officer     Commissioner of Patents and Trademarks